US012755383B2

(12) United States Patent
Choi et al.

(10) Patent No.: US 12,755,383 B2
(45) Date of Patent: Oct. 6, 2026

(54) AI-BASED APPARATUS FOR DIAGNOSING PULMONARY NODULE FROM CHEST CT IMAGE

(71) Applicants: DEEPNOID CO., LTD., Seoul (KR); PUSAN NATIONAL UNIVERSITY HOSPITAL, Busan (KR)

(72) Inventors: Woosik Choi, Incheon (KR); Taegyu Kim, Yongin-si (KR); Soobum Kim, Gwangmyeong-si (KR); Kibok Nam, Incheon (KR); Dahye Lee, Gunpo-si (KR); Hoseok I, Busan (KR)

(73) Assignees: DEEPNOID Co., Ltd., Seoul (KP); Pusan National University Hospital, Busan (KR)

( * ) Notice: Subject to any disclaimer, the term of this patent is extended or adjusted under 35 U.S.C. 154(b) by 206 days.

(21) Appl. No.: 18/822,640

(22) Filed: Sep. 3, 2024

(65) Prior Publication Data

US 2025/0191178 A1 Jun. 12, 2025

(30) Foreign Application Priority Data

Dec. 11, 2023 (KR) ........................ 10-2023-0178249

(51) Int. Cl.
*G06T 7/00* (2017.01)
*G06V 10/26* (2022.01)
(Continued)

(52) U.S. Cl.
CPC ............ *G06T 7/0012* (2013.01); *G06V 10/26* (2022.01); *G06V 10/52* (2022.01); *G06V 10/764* (2022.01);
(Continued)

(58) Field of Classification Search
CPC ......... G06T 7/0012; G06T 2207/10081; G06T 2207/20076; G06T 2207/20084;
(Continued)

(56) References Cited

U.S. PATENT DOCUMENTS

2020/0161005 A1* 5/2020 Lyman ............. G06Q 10/06315
2022/0036564 A1* 2/2022 Ye ............................. G06T 7/11
2026/0004903 A1* 1/2026 Fitzke .................... G16H 15/00

FOREIGN PATENT DOCUMENTS

CN 116030325 A * 4/2023

OTHER PUBLICATIONS

Aloraini, M., Khan, A., Aladhadh, S., Habib, S., Alsharekh, M. F., & Islam, M. (2023). Combining the transformer and convolution for effective brain tumor classification using MRI images. Applied Sciences, 13(6), 3680 (Year: 2023).*

(Continued)

*Primary Examiner* — Jennifer Mehmood
*Assistant Examiner* — Vaisali Rao Koppolu
(74) *Attorney, Agent, or Firm* — Quantum Patent Law Firm; Seongyoune Kang

(57) ABSTRACT

Proposed is an AI-based apparatus for diagnosing pulmonary nodules from a chest CT image. The apparatus includes a backbone module, a pulmonary nodule detection module, and a pulmonary nodule segmentation header, wherein the backbone module includes a convolution module composed of convolutional layers that receive the chest CT image and each generate a convolutional feature map, and a ViT-based ViT module composed of ViT layers, each of which generates a ViT feature map by receiving the convolutional feature map generated in the last convolutional layer among the convolutional layers, the pulmonary nodule detection module calculates coordinates of a suspicious pulmonary nodule area using the ViT feature map generated in the last (Continued)

ViT layer among the ViT layers, and calculates per layer classification probabilities for the respective ViT layers using the suspicious area coordinates, and the pulmonary nodule segmentation header generates a synthesized feature map.

9 Claims, 6 Drawing Sheets

(51) Int. Cl.

| | |
|---|---|
| ***G06V 10/52*** | (2022.01) |
| ***G06V 10/764*** | (2022.01) |
| ***G06V 10/766*** | (2022.01) |
| ***G06V 10/77*** | (2022.01) |
| ***G06V 10/82*** | (2022.01) |
| ***G16H 30/40*** | (2018.01) |
| ***G16H 50/20*** | (2018.01) |

(52) U.S. Cl.
CPC ........ *G06V 10/766* (2022.01); *G06V 10/7715* (2022.01); *G06V 10/82* (2022.01); *G16H 30/40* (2018.01); *G16H 50/20* (2018.01); *G06T 2207/10081* (2013.01); *G06T 2207/20076* (2013.01); *G06T 2207/20084* (2013.01); *G06T 2207/30064* (2013.01); *G06V 2201/031* (2022.01)

(58) Field of Classification Search
CPC . G06T 2207/30064; G06T 2207/20081; G06T 7/11; G06V 10/26; G06V 10/52; G06V 10/764; G06V 10/766; G06V 10/7715; G06V 10/82; G06V 2201/031; G06V 2201/03; G16H 30/40; G16H 50/20; A61B 6/5217; A61B 6/032
See application file for complete search history.

(56) References Cited

OTHER PUBLICATIONS

Kumar, S. (2023). Explainable Artificial Intelligence for Early Lung Tumor Classification Using Hybrid CNN-Transformer Networks. Frontiers in Health Informatics, 12, 484-504 (Year: 2023).*

* cited by examiner

[FIG. 1]

[FIG. 2]
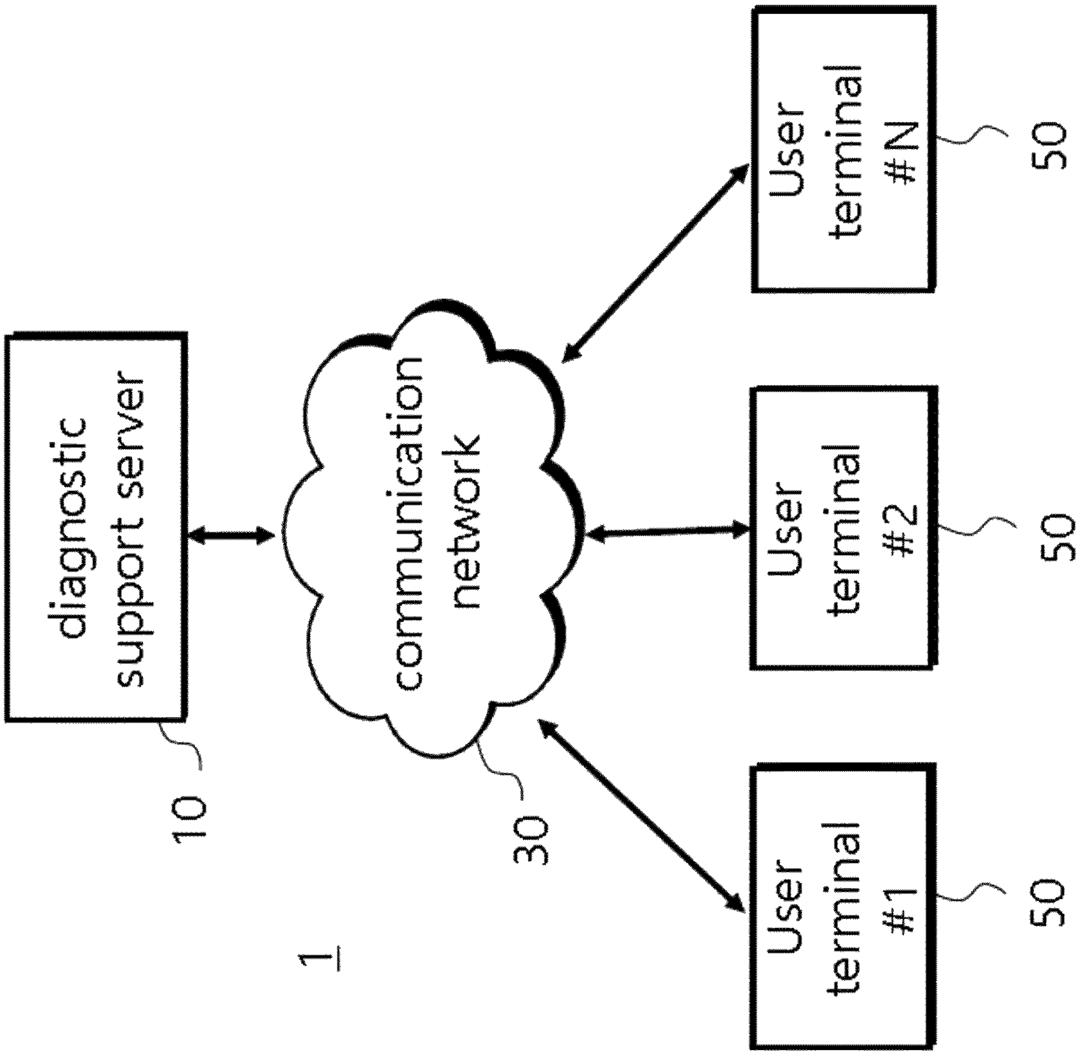

[FIG. 3]
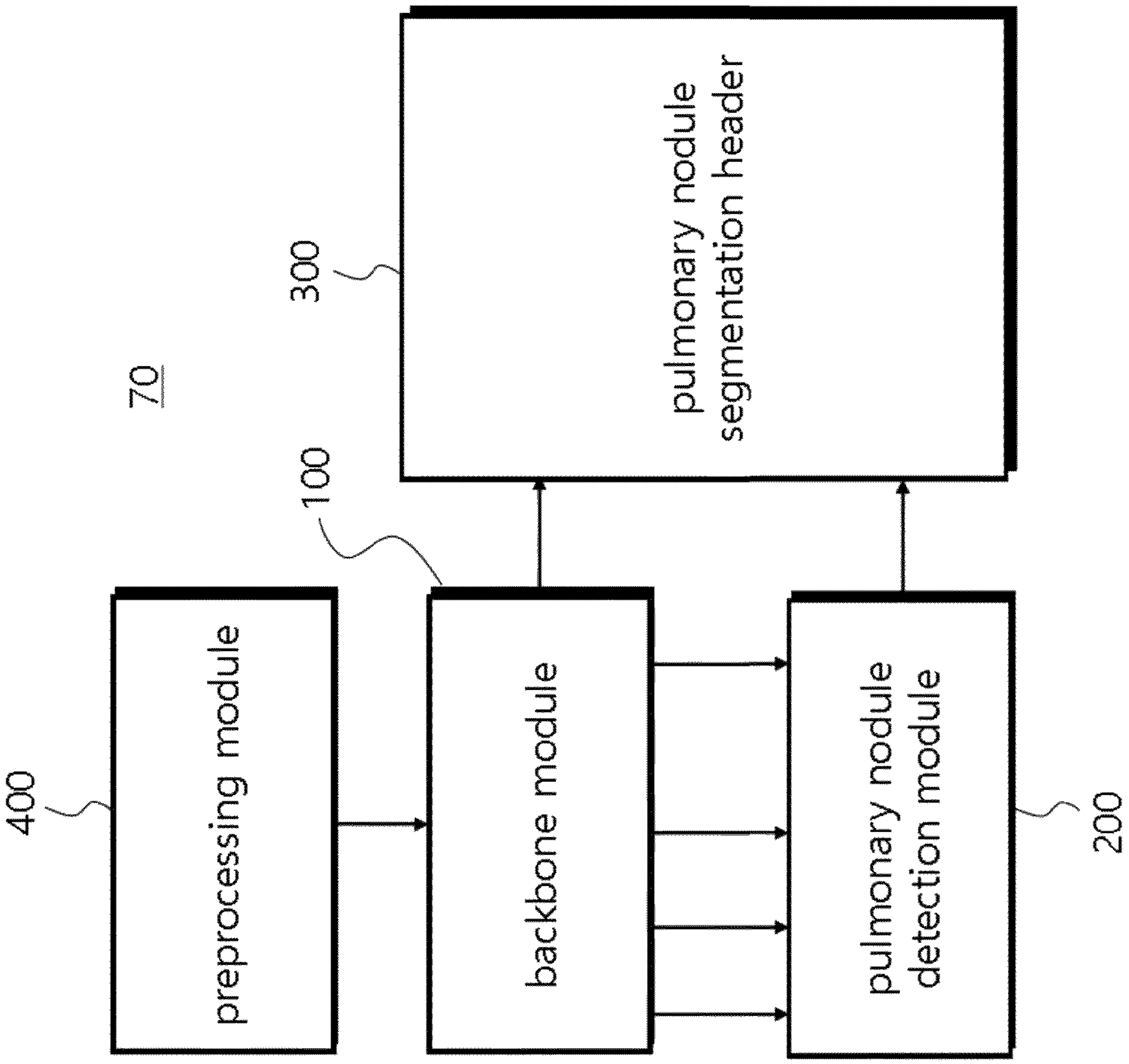

[FIG. 4]
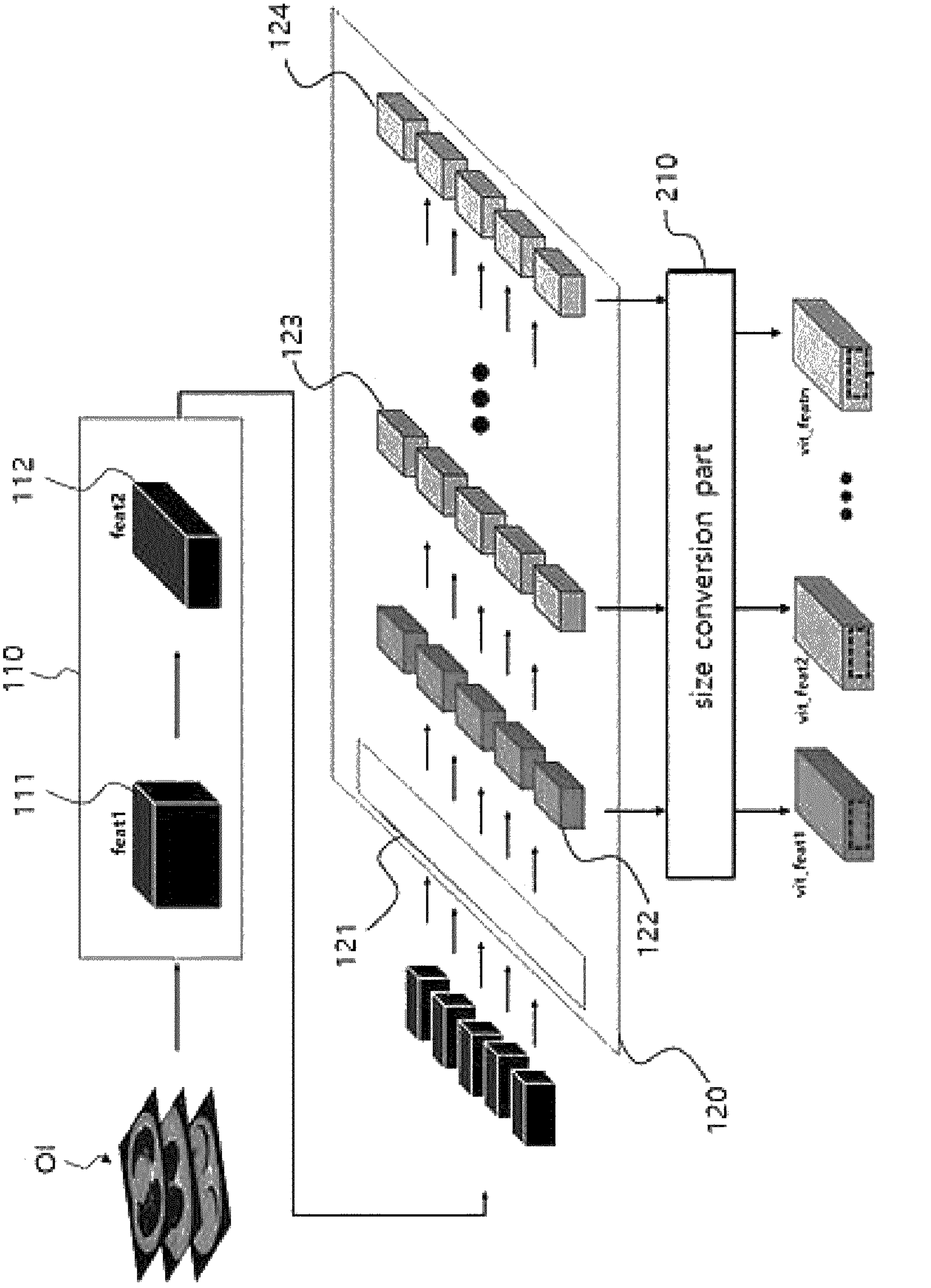

[FIG. 5]
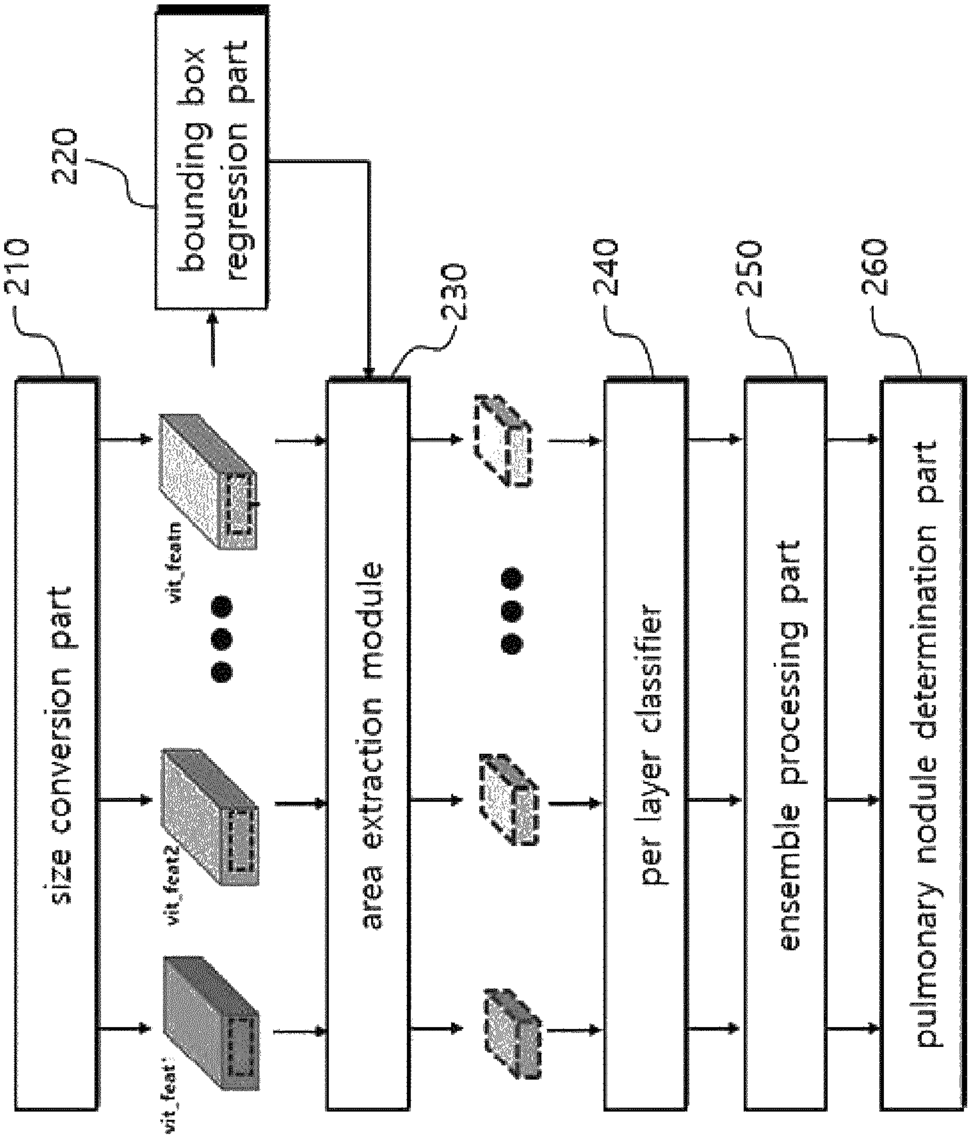

[FIG. 6]
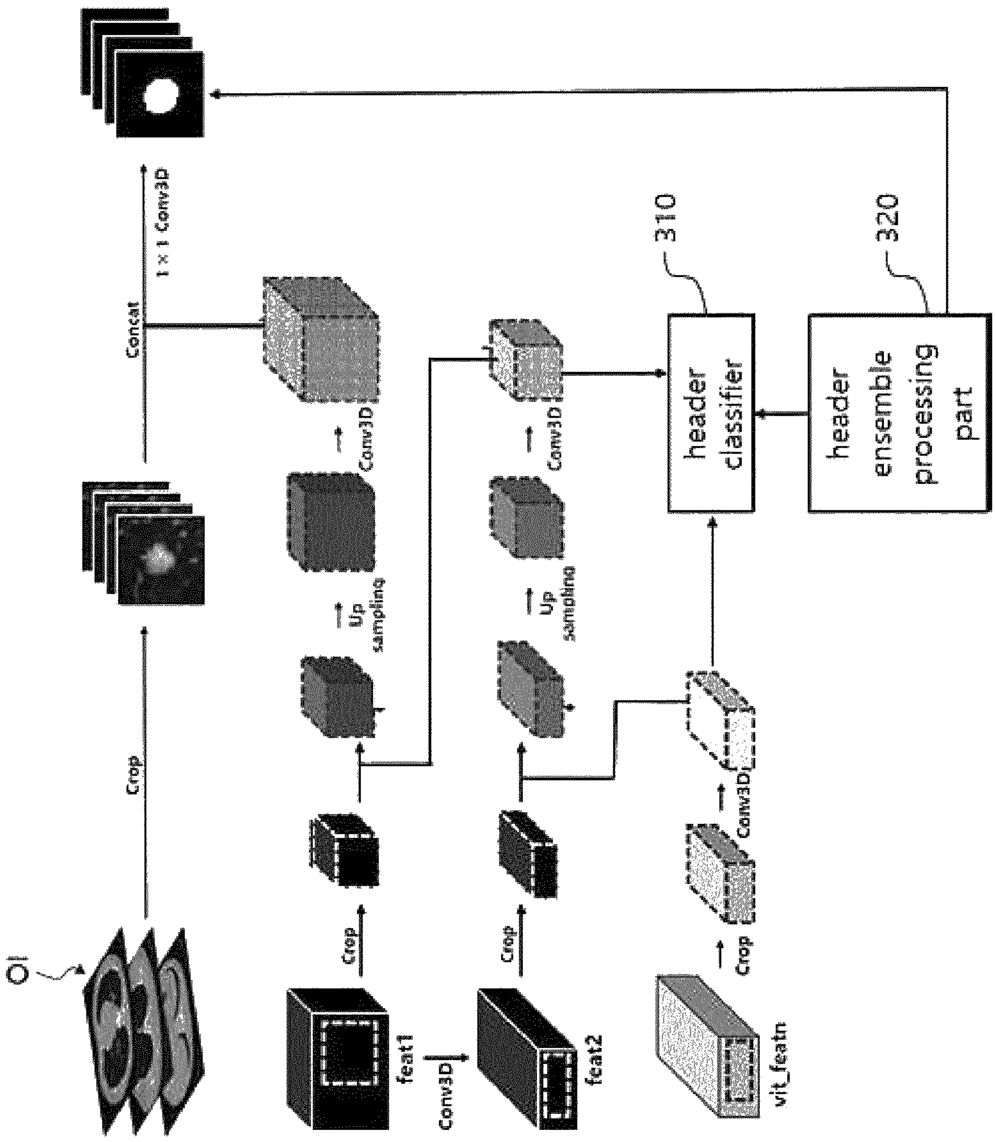

AI-BASED APPARATUS FOR DIAGNOSING PULMONARY NODULE FROM CHEST CT IMAGE

CROSS REFERENCE TO RELATED APPLICATION

The present application claims priority to Korean Patent Application No. 10-2023-0178249, filed Dec. 11, 2023, the entire contents of which is incorporated herein for all purposes by this reference.

BACKGROUND

Technical Field

The present disclosure relates to an apparatus for diagnosing pulmonary nodules and, more particularly, to an AI-based apparatus for diagnosing pulmonary nodules from a chest CT image.

Description of the Related Art

Lung cancer is the leading cause of cancer-related deaths worldwide, and because more than half of cases are discovered in advanced stages, the five-year survival rate for lung cancer is less than 20%. The most effective way to reduce lung cancer mortality is early detection and treatment.

Since lung nodules have the potential to develop into lung cancer depending on their size and morphological characteristics, it is essential to determine lung nodules through lung cancer screening for early diagnosis of lung cancer.

However, because images of chest computed tomography (CT) are three-dimensional in nature, medical staff needs to check all CT scan slides to detect lung nodules and classify malignant (cancerous) lung nodules, and thus there is a possibility of false-positive results.

In fact, among the lung nodule lesions that were found to be positive in the 2011 National Lung Screening Trial (NLST), only 3.6% were ultimately diagnosed as lung cancer, showing a high false-positive rate of 96.4%.

For accurate interpretation of low-dose CT images, an experienced expert (radiologist) is needed, but considering the expected number of CT examinations and the time and effort required to read and interpret the findings, there is a great burden on the medical work of these radiologists.

Although artificial intelligence (AI)-assisted lung nodule detection models have been proposed recently, many false positives are detected in the lung nodule detection models. Accordingly, various models are being developed to reduce false positives, but the limitation that there are still many false positives exists.

Since chest CT images are composed of a large number of slides, in the case of models targeting chest CT images, the large amount of calculation and long analysis time have been raised as problems in AI-based lung nodule detection models. Moreover, as shown in FIG. 1, pulmonary nodules are generally small in size and sometimes asymptomatic, making diagnosis difficult. At this time, FIG. 1*a* is a chest CT image, and FIG. 1*b* is an enlarged image of a lung nodule area.

Most segmentation models that have achieved high performance in recent years primarily perform bounding box regression and classification. Only when an object marked by a bounding box is determined to be a target object through classification, segmentation is carried out based on the coordinates of the corresponding bounding box, thereby reducing analysis time and improving accuracy.

Meanwhile, a vision transformer (ViT) combines a model (transformer) developed for natural language processing tasks with image processing, and most models that have recently achieved state-of-the-art (SOTA) performance leverage Transformer architecture.

A transformer is an attention network-based model that divides an image into several small patches and learns the dependencies between the patches, showing superior performance compared to existing convolutional neural network (CNN)-based image processing models.

However, in a ViT model, feature maps created from passing through layers have different information, and as more layers are passed through, there is a risk that information from previous stages will be lost.

If classification is performed only on one feature map, especially the feature map of the last stage, the classification is made while information from a previous stage or the original is lost, making it difficult to expect accurate results.

SUMMARY

Accordingly, the present disclosure has been made keeping in mind the above problems occurring in the related art, and the present disclosure is intended to provide an AI-based apparatus for diagnosing pulmonary nodules from a chest CT image, which enables more accurate diagnosis of pulmonary nodules by minimizing loss of information from previous stages or the original while being based on ViT.

In order to achieve the above objective, according to an aspect of the present disclosure, there is provided an AI-based apparatus for diagnosing pulmonary nodules from a chest CT image, the apparatus including: a backbone module, a pulmonary nodule detection module, and a pulmonary nodule segmentation header, wherein the backbone module may include a convolution module composed of convolutional layers that receive the chest CT image and each generate a convolutional feature map, and a ViT-based ViT module composed of ViT layers, each of which generates a ViT feature map by receiving the convolutional feature map generated in the last convolutional layer among the convolutional layers, the pulmonary nodule detection module may calculate coordinates of a suspicious pulmonary nodule area using the ViT feature map generated in the last ViT layer among the ViT layers, calculate per layer classification probabilities for the respective ViT layers using the suspicious area coordinates, and infer whether there is a pulmonary nodule through ensembling of the per layer classification probabilities and calculating a pulmonary nodule classification probability, and the pulmonary nodule segmentation header may generate a synthesized feature map by extracting respective suspicious areas from the convolutional feature map generated in each convolutional layer and the ViT feature map generated in the last ViT layer using the suspicious area coordinates when the pulmonary nodule is inferred by the pulmonary nodule detection module, calculate a final classification probability through ensembling of a pulmonary nodule classification probability for the synthesized feature map and a pulmonary nodule classification probability for the suspicious area extracted from the ViT feature map generated in the last ViT layer, and create a segmentation image of the chest CT image using the synthesized feature map and the final classification probability.

In this case, the pulmonary nodule detection module may include: a bounding box regression part that calculates the suspicious area coordinates from the ViT feature map generated in the last ViT layer; an area extraction module that extracts respective suspicious areas from the ViT feature maps generated in the ViT layers using the suspicious area coordinates; a per layer classifier that receives the suspicious area extracted by the area extraction module and calculates the per layer classification probabilities for the respective ViT layers; an ensemble processing part that calculates the pulmonary nodule classification probability through ensembling of the per layer classification probabilities; and a pulmonary nodule determination part that determines whether there is a pulmonary nodule on the basis of the pulmonary nodule classification probability calculated by the ensemble processing part.

In this case, the pulmonary nodule detection module may further include: a size conversion part that converts a size of the ViT feature map generated for each of the ViT layers to the same size.

In addition, the ensemble processing part may calculate an average value of the per layer classification probabilities as the pulmonary nodule classification probability.

In addition, the per layer classifier may calculate the per layer classification probabilities by organizing the respective suspicious areas of the ViT feature maps generated in the ViT layers in a row and passing the organized suspicious areas through a fully connected layer.

In addition, the pulmonary nodule segmentation header may generate the synthesized feature map through synthesis with the suspicious area extracted from the convolutional feature map generated in the last convolutional layer as a first synthesized feature map is generated by synthesizing the suspicious area extracted from the convolutional feature map generated in the last convolutional layer among the convolutional layers with the suspicious area extracted from the ViT feature map generated from the last ViT layer, and then a second synthesized map is generated by synthesizing the suspicious area extracted from the convolutional feature map generated in the convolutional layer immediately before the last convolutional layer with the first synthesized feature map.

In addition, the pulmonary nodule segmentation header may include: a header classifier that calculates a header classification probability of the synthesized feature map generated from the first synthesized feature map, and a header classification probability of the ViT feature map generated in the last ViT layer; and a header ensemble processing part that calculates an average value of the header classification probabilities calculated by the header classifier as the final classification probability.

In addition, the pulmonary nodule segmentation header may synthesize the suspicious area extracted from the convolutional feature map generated from the first convolutional layer with the synthesized feature map to create an m-th synthesized feature map, create a final feature map by synthesizing an original suspicious area extracted from the chest CT image using the suspicious area coordinates with the m-th synthesized feature map, and create a segmentation image for the chest CT image using the final feature map and the final classification probability.

In addition, the pulmonary nodule segmentation header may create a mask image by passing the final feature map through a 1×1 convolutional layer, and create the mask image or zero image as the segmentation image according to the final classification probability.

According to the present disclosure, due to the above configuration, by calculating the pulmonary nodule classification probability through an ensemble process in a pulmonary nodule detection module and a pulmonary nodule segmentation header, it is possible to solve the problem that a large number of false positives are discovered in conventional AI-based models, which degrades the performance of lung nodule detection models.

In addition, because a detection model is implemented in one stage rather than multiple stages, reading time can be shortened, and the performance of not only lung nodule detection but also lung nodule segmentation can be improved.

Furthermore, by using feature maps generated from previous layers in calculating a pulmonary nodule classification probability or generating a pulmonary nodule segmentation image, the problem of information loss, which occurs as the layer gets deeper, can be resolved.

BRIEF DESCRIPTION OF THE DRAWINGS

The above and other objectives, features, and other advantages of the present disclosure will be more clearly understood from the following detailed description when taken in conjunction with the accompanying drawings, in which:

FIG. 2 is a view showing an example of configuration of a pulmonary nodule diagnosis system according to an embodiment of the present disclosure;

FIG. 3 is a view showing an example of configuration of an apparatus for diagnosing pulmonary nodules according to an embodiment of the present disclosure;

FIG. 4 is a view showing the structure of a backbone module of FIG. 3;

FIG. 5 is a view showing the structure of a pulmonary nodule detection module of FIG. 3; and FIG. 6 is a view showing the structure of a pulmonary nodule segmentation header of FIG. 3.

DETAILED DESCRIPTION

Figure 1:
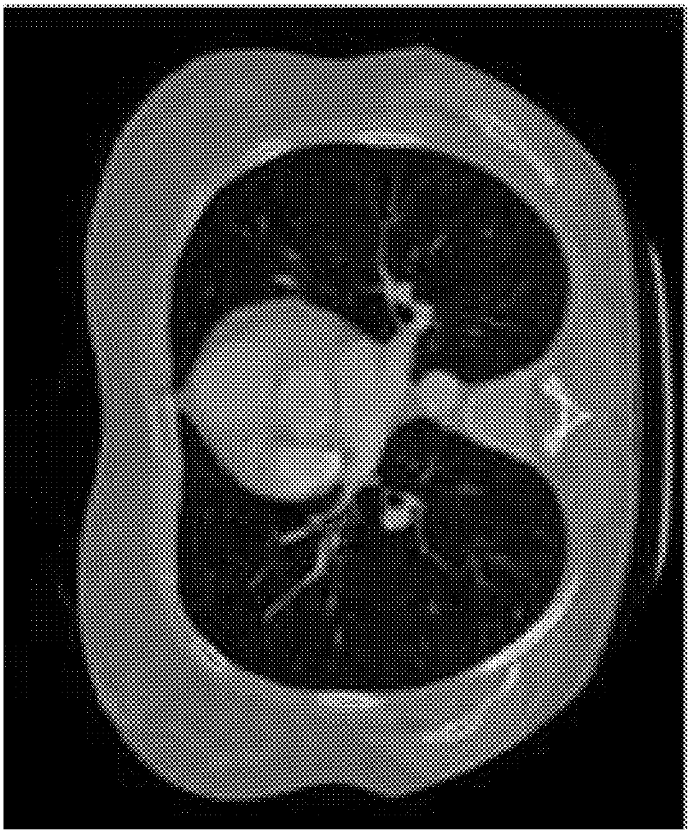
FIGS. 1*a* and 1*b* are views showing an example of a chest CT image.
Figure 1:
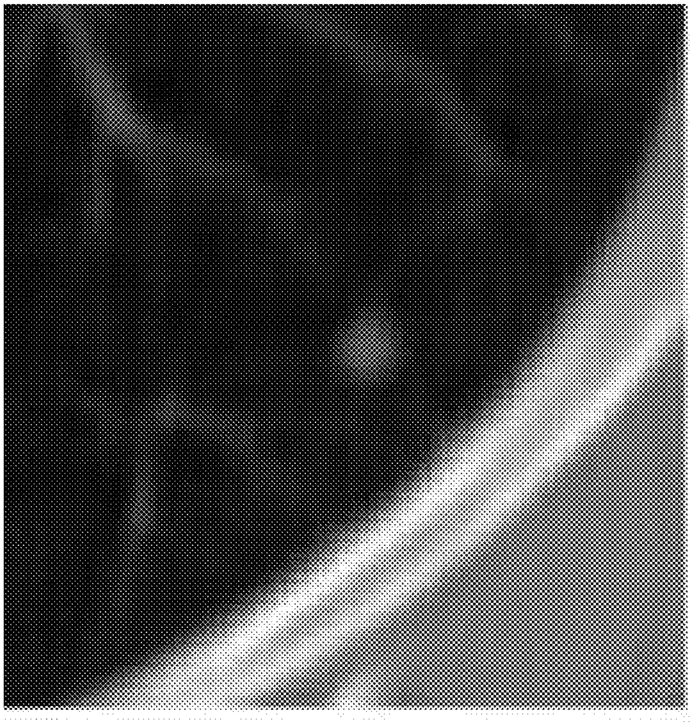

Since the present disclosure may be modified in various ways and may have various embodiments, specific embodiments will be illustrated in the drawings and described in detail.

However, this is not intended to limit the present disclosure to specific embodiments, and should be understood to include all changes, equivalents, and substitutes included in the spirit and technical scope of the present disclosure.

The terms used in this application are only used to describe specific embodiments, and are not intended to limit the present disclosure, and the singular expression may include a plural expression unless the context clearly indicates otherwise. In addition, it should be understood that in the present disclosure, terms such as "comprise" or "have" are intended to designate that a feature, number, step, operation, component, part, or combination thereof described in the specification exists, and do not preclude the possibility of addition or existence of one or more other features or numbers, steps, operations, components, parts, or combinations thereof.

Unless otherwise defined, all terms used herein, including technical or scientific terms, have the same meaning as commonly understood by a person skilled in the art. Terms such as those defined in the commonly used dictionaries should be construed as having meanings consistent with the meanings in the context of the related art and shall not be construed in ideal or excessively formal meanings unless expressly defined in this application.

Hereinafter, embodiments according to the present disclosure will be described in detail with reference to the attached drawings.

FIG. 2 is a view showing an example of configuration of a pulmonary nodule diagnosis system according to an embodiment of the present disclosure.

Referring to FIG. 2, a pulmonary nodule diagnosis system according to an embodiment of the present disclosure may include a diagnostic support server 10, and a plurality of user terminals 50.

Each user terminal 50 may be connected to the diagnostic support server 10 through a communication network 30 such as the Internet, to communicate with each other. In an embodiment, the user terminal 50 may include an information processing terminal such as a computer deployed in a hospital.

In this case, an apparatus for diagnosing pulmonary nodules 70 according to an embodiment of the present disclosure may be installed in the diagnostic support server 10. In addition, each user may access the diagnostic support server 10 using his or her user terminal 50 and use the apparatus for diagnosing pulmonary nodules 70.

As another example, the apparatus for diagnosing pulmonary nodules 70 may be installed in the user terminal 50. In addition, a user may use the apparatus for diagnosing pulmonary nodules 70 installed in his or her user terminal 50.

To this end, the apparatus for diagnosing pulmonary nodules 70 may be implemented in the form of a computer program capable of diagnosing pulmonary nodules and installed on the diagnostic support server 10 or the user terminal 50.

FIG. 3 is a view showing an example of configuration of the apparatus for diagnosing pulmonary nodules 70 according to an embodiment of the present disclosure. In the embodiment shown in FIG. 3, the apparatus for diagnosing pulmonary nodules 70 is installed in the diagnostic support server 10.

The apparatus for diagnosing pulmonary nodules 70 according to an embodiment of the present disclosure is configured to diagnose pulmonary nodules from a chest CT image OI, for example. As an example, the chest CT image OI may be input in DICOM format.

Referring to FIG. 3, the apparatus for diagnosing pulmonary nodules 70 according to an embodiment of the present disclosure may include a backbone module 100, a pulmonary nodule detection module 200, and a pulmonary nodule segmentation header 300. The apparatus for diagnosing pulmonary nodules 70 may also include a preprocessing module 400.

The preprocessing module 400 according to an embodiment of the present disclosure may preprocess the chest CT image OI for input to the backbone module 100. As an example, the preprocessing module 400 may normalize the chest CT image OI using a pre-registered normalization algorithm. In addition, the preprocessing module 400 may resize the normalized chest CT image OI to a pre-registered 3D size.

As an example, normalization may be performed by using [Equation 1].

$$I_N = (I - Min)\frac{newMax - newMin}{Max - Min} + newMin \qquad \text{[Equation 1]}$$

In [Equation 1], I is the pixel value before normalization, Min and Max are the minimum and maximum values of the range before normalization, newMin and newMax are the minimum and maximum values of the range after normalization, and $I_N$ is the pixel value after normalization.

The chest CT image OI preprocessed by the preprocessing module 400 as described above is input to the backbone module 100.

The backbone module, the pulmonary nodule detection module, and the pulmonary nodule segmentation header 300 according to an embodiment of the present disclosure are learning models learned based on artificial intelligence, and diagnose the presence of lung nodules inferred from the input chest CT image OI.

The backbone module 100 according to an embodiment of the present disclosure is configured based on Vision Transformer (ViT). The backbone module 100 according to an embodiment of the present disclosure receives the chest CT image OI and generates a feature map. In an embodiment of the present disclosure, the 3D chest CT image OI is targeted, and 3D-based ViT is applied to the backbone module 100, and the components to be described later are also driven on a 3D basis.

FIG. 4 is a view showing an example of the structure of the backbone module 100 according to an embodiment of the present disclosure.

Referring to FIG. 4, the backbone module 100 according to an embodiment of the present disclosure may include a convolution module and a ViT-based ViT module 120.

The convolution module according to an embodiment of the present disclosure may include a plurality of convolutional layers. FIG. 4 shows an example consisting of two convolutional layers, but the number is not limited to thereto.

The chest CT image OI input to the convolution module passes through the convolutional layers and generates respective feature maps (hereinafter referred to as "convolutional feature maps feat1 and feat2") in the convolutional layers. At this time, the convolutional feature map feat2 generated in the last convolutional layer 112 is delivered to the ViT module 120. As an example, the convolutional feature maps feat1 and feat2 generated in the respective convolutional layers 111 and 112 may be cropped to the same size and patched.

The ViT module 120 according to an embodiment of the present disclosure includes a plurality of ViT layers 122, 123, and 124. In FIG. 4, it is illustrated that n ViT layers 122, 123, and 124 constitute the ViT module 120.

The convolutional feature map feat2 passes through the plurality of ViT layers 122, 123, and 124, and feature maps (hereinafter referred to as "ViT feature map vit_feat1, vit_feat2, vit_featn") are generated in the ViT layers 122, 123, and 124, respectively. In this case, for ViT-based operation, patch embedding and position embedding may be performed on the convolutional feature map feat2 input to the ViT module 120 while passing through a ViT-based embedding part 121.

The pulmonary nodule detection module 200 according to an embodiment of the present disclosure may calculate coordinates of a suspicious pulmonary nodule area using the ViT feature map vit_featn generated in the last ViT layer 124 among the plurality of ViT layers 122, 123, and 124.

The pulmonary nodule detection module 200 calculates the per layer classification probability for each of the ViT layers 122, 123, and 124 using the coordinates of the suspicious area, and calculates the pulmonary nodule classification probability through ensembling of the per layer classification probabilities. In addition, the pulmonary nodule detection module 200 determines whether there is a pulmonary nodule on the basis of the pulmonary nodule classification probability.

FIG. 5 is a view showing the structure of the pulmonary nodule detection module 200 according to an embodiment of the present disclosure.

Referring to FIG. 5, the pulmonary nodule detection module 200 according to an embodiment of the present disclosure may include a size conversion part 210, a bounding box regression part 220, an area extraction module 230, a per layer classifier 240, an ensemble processing part 250, and a pulmonary nodule determination part 260.

The size conversion part 210 according to an embodiment of the present disclosure converts the sizes of the ViT feature maps vit_feat1, vit_feat2, and vit_featn generated for the ViT layer 122, 123, and 124, respectively, to be the same.

As an example, since the ViT feature maps vit_feat1, vit_feat2, and vit_featn generated for the ViT layer 122, 123, and 124, respectively, have the form of cropped patches of the same size, the size conversion part 210 may combine sub-feature maps in the form of patches in the reverse order of the previous cropping algorithm. In addition, the size conversion part 210 may convert the sizes of the combined ViT feature maps vit_feat1, vit_feat2, and vit_featn to be the same.

Due to this, when extracting a suspicious area by using the suspicious area coordinates, which will be described later, extraction from the corresponding location with the same scale may be possible.

The bounding box regression part 220 calculates the coordinates of a suspicious area from the ViT feature map vit_featn generated in the last ViT layer 124 among the plurality of ViT layers 122, 123, and 124. At this time, the bounding box regression part 220 calculates the coordinates of an area suspected to be a pulmonary nodule as the suspicious area coordinates via bounding box regression.

The area extraction module 230 uses the suspicious area coordinates calculated by the bounding box regression part 220 to extract a suspicious area from the ViT feature maps vit_feat1, vit_feat2, and vit_featn generated for the respective ViT layers 122, 123, and 124.

The per layer classifier 240 may receive information on the suspicious area extracted from the ViT feature maps vit_feat1, vit_feat2, and vit_featn generated in the respective ViT layers 122, 123, and 124 by the area extraction module 230, and calculate the classification probability for each of the ViT layers 122, 123, and 124.

As an example, the per layer classifier 240 may calculate the per layer classification probability by organizing suspicious areas of the ViT feature maps vit_feat1, vit_feat2, and vit_featn generated in the respective ViT layers 122, 123, and 124 in a row and passing the organized suspicious areas through a fully connected layer.

The ensemble processing part 250 calculates the pulmonary nodule classification probability through ensembling of the per layer classification probabilities calculated for the ViT layers 122, 123, and 124 to. As an example, the ensemble processing part 250 may calculate an average value of classification probabilities for each layer as the pulmonary nodule classification probability, which may be expressed as [Equation 2].

$$p = \frac{(p_{F1} + p_{F2} + \ldots + p_{FN})}{N} \quad \text{[Equation 2]}$$

In [Equation 2], FN is the Nth ViT feature map vit_feat1, vit_feat2, or vit_featn, $p_{FN}$ is the per layer classification probability of the Nth ViT feature map vit_feat1, vit_feat2, or vit_featn, N is the number of ViT layers 122, 123, and 124, and p is the pulmonary nodule classification probability.

As described above, when the pulmonary nodule classification probability is calculated by the ensemble processing part 250, the pulmonary nodule determination part 260 may infer whether there is a pulmonary nodule from the pulmonary nodule classification probability. At this time, the pulmonary nodule determination part 260 may determine whether there is a pulmonary nodule on the basis of a preset reference probability.

Meanwhile, the pulmonary nodule segmentation header 300 according to an embodiment of the present disclosure generates a segmentation image of the chest CT image OI using the suspicious area coordinates calculated by the pulmonary nodule detection module 200. At this time, in the embodiment of the present disclosure, the pulmonary nodule segmentation header 300 generates a segmentation image for an area determined to be a pulmonary nodule by the pulmonary nodule detection module 200.

FIG. 6 is a view showing the structure of the pulmonary nodule segmentation header 300 according to an embodiment of the present disclosure.

Referring to FIG. 6, when a pulmonary nodule is determined by the pulmonary nodule detection module 200, the pulmonary nodule segmentation header 300 extracts, by using the suspicious area coordinates, suspicious areas from the convolutional feature maps feat1 and feat2 generated in the respective convolutional layers and the ViT feature map vit_featn generated in the last ViT layer 124, and creates a synthesized feature map.

To be specific, the pulmonary nodule segmentation header 300 synthesizes a suspicious area extracted from the convolutional feature map feat2 generated in the last convolutional layer 112 with a suspicious area extracted from the ViT feature map vit_featn generated in the last ViT layer 124 and creates a first synthesized feature map.

In this case, the suspicious area extracted from the ViT feature map vit_featn generated in the last ViT layer passes through a 3D convolutional layer, may be extracted as a feature map, and synthesized with the suspicious area extracted from the convolutional feature map feat2 generated in the last convolutional layer 112, and then up-sampled to gradually increase in size, passed through a 3D convolutional layer, extracted s a feature map, and created as the first synthesized feature map.

Thereafter, the pulmonary nodule segmentation header 300 generates a second synthesized map by synthesizing the suspicious area extracted from the convolutional feature map generated in the convolutional layer 111 immediately before the last convolutional layer with the first synthesized feature map.

In this case, the suspicious area extracted from the convolutional feature map feat1 generated in the convolutional layer 111 immediately before the last convolutional layer 112 may be synthesized with the first synthesized feature map, and then up-sampled to gradually increase in size, passed through a 3D convolutional layer, extracted as a feature map, and created as the second synthesized map.

In the embodiment of the present disclosure, the synthesized feature maps are generated through synthesis with the suspicious area extracted from the convolutional feature map feat2 generated in the second convolutional layer 112 among the plurality of convolutional layers constituting the convolution module 110.

To be specific, when the convolution module 110 is composed of m convolution layers 111 and 112, an m−1st synthesized map may be generated from a first synthesized map in the same manner as above. In the embodiment of the present disclosure, since two convolutional layers 111 and 112 constitute the convolution module 110, by synthesizing suspicious areas extracted from the convolutional feature map feat2 and the ViT feature map vit_featn generated from the second convolutional layer 112 and the last ViT layer 124, respectively, one synthesized feature map is created.

The pulmonary nodule segmentation header 300 according to an embodiment of the present disclosure may calculate the final classification probability through ensembling of the pulmonary nodule classification probability for the synthesized feature map, generated from the first synthesized feature map, that is, the m−1st synthesized map, and the pulmonary nodule classification probability for the suspicious area extracted from the ViT feature map vit_featn generated in the last ViT layer 124.

To this end, the pulmonary nodule segmentation header 300 may include a header classifier 310, and may calculate, via classification, the pulmonary nodule classification probability for the synthesized feature map generated from the first synthesized feature map, that is, the m−1st synthesized map, and the pulmonary nodule classification probability for the suspicious area extracted from the ViT feature map vit_featn generated in the last ViT layer 124.

To this end, the pulmonary nodule segmentation header 300 may include a header ensemble processing part 320 that calculates an average value of the header classification probabilities calculated by the header classifier 310 as the final classification probability.

Meanwhile, the pulmonary nodule segmentation header 300 uses the synthesized feature map and the final classification probability to generate a segmentation image of the chest CT image OI.

To be specific, the pulmonary nodule segmentation header 300 synthesizes the suspicious area extracted from the convolutional feature map feat1 generated from the first convolutional layer 111 with the synthesized feature map, that is, the m−1st synthesized feature map to create an m-th synthesized feature map.

Thereafter, the pulmonary nodule segmentation header 300 extracts an original suspicious area from the chest CT image OI using the suspicious area coordinates, and generates the final feature map by synthesizing the original suspicious area with the m-th synthesized feature map.

In addition, the pulmonary nodule segmentation header 300 creates a segmentation image for the chest CT image OI using the final classification probability and the final feature map. As an example, the pulmonary nodule segmentation header 300 creates a mask image by passing the final feature map through a 1×1 convolutional layer, and creates the mask image or zero image as the segmentation image according to the final classification probability.

To be specific, the 1×1 convolutional layer may include an activation function such as a sigmoid function to convert the final feature map with a probability value for each pixel to have values between 0 and 1 by using an activation function and create a mask image in binary form by converting the value of each pixel to 1 or 0 based on a preset reference value, for example, 0.5.

In addition, when the final classification probability is reflected by dividing the values into 0 and 1, that is, non-pulmonary nodules and pulmonary nodules, based on a specific reference value, a mask image or zero image, that is, a segmentation image of a black and white image may be output.

Due to the above configuration, by calculating the pulmonary nodule classification probability through an ensemble process in a pulmonary nodule detection module and a pulmonary nodule segmentation header, it is possible to solve the problem that a large number of false positives are discovered in conventional AI-based models, which degrades the performance of lung nodule detection models.

In addition, because a detection model is implemented in one stage rather than multiple stages, reading time can be and the performance of not only lung nodule shortened, detection but also lung nodule segmentation may be improved.

In addition, by using feature maps from previous layers in calculating a pulmonary nodule classification probability or generating a pulmonary nodule segmentation image, the problem of information loss, which occurs as the layer gets deeper, may be resolved.

Furthermore, while conventionally, a 3D feature map is up-sampled to the same size as an original pulmonary image to generate a pulmonary nodule segmentation image, in the present disclosure, up-sampling is performed to the size of the original suspicious area extracted from the chest CT image OI based on the suspicious area coordinates, thereby reducing the amount of calculation and analysis time.

Although specific embodiments of the present disclosure have been shown and described, those skilled in the art who have ordinary knowledge in the technical field to which the present disclosure pertains will recognize that modifications can be made to this embodiment without departing from the principles or spirit of the present disclosure. The scope of the present disclosure will be defined by the appended claims and their equivalents.

What is claimed is:

1. An AI-based apparatus for diagnosing pulmonary nodules from a chest CT image, the apparatus comprising:

a backbone module;

a pulmonary nodule detection module; and a pulmonary nodule segmentation header, wherein the backbone module comprises:

a convolution module composed of convolutional layers that receive the chest CT image and each generate a convolutional feature map; and a ViT-based ViT module composed of ViT layers, each of which generates a ViT feature map by receiving the convolutional feature map generated in the last convolutional layer among the convolutional layers, the pulmonary nodule detection module calculates coordinates of a suspicious pulmonary nodule area using the ViT feature map generated in the last ViT layer among the ViT layers, calculates per layer classification probabilities for the respective ViT layers using the suspicious area coordinates, and infers whether there is a pulmonary nodule through ensembling of the per layer classification probabilities and calculating a pulmonary nodule classification probability, and the pulmonary nodule segmentation header generates a synthesized feature map by extracting respective suspicious areas from the convolutional feature map generated in each convolutional layer and the ViT feature map generated in the last ViT layer using the suspicious area coordinates when the pulmonary nodule is inferred by the pulmonary nodule detection module, calculates a final classification probability through ensembling of a pulmonary nodule classification probability for the synthesized feature a pulmonary map and nodule classification probability for the suspicious area extracted from the ViT feature map generated in the last ViT layer, and creates a segmentation image of the chest CT image using the synthesized feature map and the final classification probability.

2. The apparatus of claim 1, wherein the pulmonary nodule detection module comprises:

a bounding box regression part that calculates the suspicious area coordinates from the ViT feature map generated in the last ViT layer;

an area extraction module that extracts respective suspicious areas from the ViT feature maps generated in the ViT layers using the suspicious area coordinates;

a per layer classifier that receives the suspicious area extracted by the area extraction module and calculates the per layer classification probabilities for the respective ViT layers;

an ensemble processing part that calculates the pulmonary nodule classification probability through ensembling of the per layer classification probabilities; and a pulmonary nodule determination part that determines whether there is a pulmonary nodule on the basis of the pulmonary nodule classification probability calculated by the ensemble processing part.

3. The apparatus of claim 2, wherein the pulmonary nodule detection module further comprises:

a size conversion part that converts a size of the ViT feature map generated for each of the ViT layers to the same size.

4. The apparatus of claim 2, wherein the ensemble processing part calculates an average value of the per layer classification probabilities as the pulmonary nodule classification probability.

5. The apparatus of claim 2, wherein the per layer classifier calculates the per layer classification probabilities by organizing the respective suspicious areas of the ViT feature maps generated in the ViT layers in a row and passing the organized suspicious areas through a fully connected layer.

6. The apparatus of claim 1, wherein the pulmonary nodule segmentation header generates the synthesized feature map through synthesis with the suspicious area extracted from the convolutional feature map generated in the last convolutional layer as a first synthesized feature map is generated by synthesizing the suspicious area extracted from the convolutional feature map generated in the last convolutional layer among the convolutional layers with the suspicious area extracted from the ViT feature map generated from the last ViT layer, and then a second synthesized map is generated by synthesizing the suspicious area extracted the from convolutional feature map generated in the convolutional layer immediately before the last convolutional layer with the first synthesized feature map.

7. The apparatus of claim 6, wherein the pulmonary nodule segmentation header comprises:

a header classifier that calculates a header classification probability of the synthesized feature map generated from the first synthesized feature map, and a header classification probability of the ViT feature map generated in the last ViT layer; and header ensemble processing part that calculates an average value of the header classification probabilities calculated by the header classifier as the final classification probability.

8. The apparatus of claim 6, wherein the pulmonary nodule segmentation header synthesizes the suspicious area extracted from the convolutional feature map generated from the first convolution layer with the synthesized feature map to create an m-th synthesized feature map, creates a final feature map by synthesizing an original suspicious area extracted from the chest CT image using the suspicious area coordinates with the m-th synthesized feature map, and creates a segmentation image for the chest CT image using the final feature map and the final classification probability.

9. The apparatus of claim 8, wherein the pulmonary nodule segmentation header creates a mask image by passing the final feature map through a 1×1 convolutional layer, and creates the mask image or zero image as the segmentation image according to the final classification probability.

* * * * *